United States Patent [19]

Cavazza

[11] 4,255,449

[45] Mar. 10, 1981

[54] METHOD OF TREATING ABNORMAL LIPOPROTE IN RATIOS

[76] Inventor: Claudio Cavazza, P.O. Box 23, Chiasso, Switzerland

[21] Appl. No.: 83,418

[22] Filed: Oct. 10, 1979

Related U.S. Application Data

[63] Continuation-in-part of Ser. No. 9,134, Feb. 5, 1979, abandoned.

[30] Foreign Application Priority Data

Feb. 3, 1978 [IT] Italy .............................. 47900 A/78
May 15, 1978 [IT] Italy .............................. 49353 A/78

[51] Int. Cl.$^3$ ............................................ A61K 31/205
[52] U.S. Cl. ..................................... 424/316; 424/319
[58] Field of Search ............................... 424/316, 319

[56] References Cited

U.S. PATENT DOCUMENTS

| | | | |
|---|---|---|---|
| 3,810,994 | 5/1974 | Wiegand | 424/316 |
| 3,968,241 | 7/1976 | Defelice | 424/319 |
| 4,032,641 | 6/1977 | Chibata | 424/266 |
| 4,075,352 | 2/1978 | Defelice | 424/319 |

OTHER PUBLICATIONS

Strack, Protides of the Biological Fluids, 7th Coll., Bruges, 1959, pp. 263-267.
Frohlich, Metabolism, vol. 27, No. 5, 1978, pp. 555-561.
Frohlich et al, Metabolism, vol. 27, No. 5, May 1978, pp. 555-561.
Castelli et al, Circulation, vol. 55, 1977, pp. 767-772.
Strack et al, Reprint from "Protides of the Biological Fluids", (Proceedings, 7th Colloquium, Bruges 1959), Elsevier Pub., 1960, pp. 263-267.
Cardiovascular Risk Mgt.-Current Perspectives, Smith, Kline & French Labs., Cardiovascular Forum, pp. 1-16.
Cayen, Ann. Rep. in Med. Chem. Cpt. 19, Acd. Press, 1979, pp. 198-208.
Havel, Circulation, vol. 60, Jul. 1979, pp. 1-3.
Mjøs, Scand. J. Clin. Lab. Invest., vol. 37, 1977, pp. 191-193.
Opie, The Lancet, Jan. 27, 1973, pp. 192-195.
Grotto et al, Atherosclerosis Rev. Raven Press, N. Y., vol. 3, 1978, pp. 231-242.
Gordon, Amer. J. Med. 62 pp. 707-714 (1977).
Gemelli, Boll. Soc. Ital. Bio. Sper., vol. 50, 1974, pp. 667-672, (Chem. Abs., vol. 82, 1975, Ab. No. 149492n).
Branca, Chem. Abs., vol. 87, 1977, Ab. No. 100942y.
Fritz, Chem. Abs., vol. 59, 1963, Ab. No. 10403.
Fraenkel, Vitamins & Hormones, Acd. Press, N.Y., vol. XV, 1957, pp. 73-118.
Preziosi, Lipid. Pharm. Med. Chem. Series, vol. 2, 1964, Acd. Press, N. Y., pp. 446-450.

*Primary Examiner*—Anna P. Fagelson
*Attorney, Agent, or Firm*—Jacobs & Jacobs

[57] ABSTRACT

Abnormally high ratios of low density and very low density lipoproteins to high density lipoproteins, an etiological factor in vascular conditions, are reduced by oral or parenteral administration of carnitine which increases the level of high density lipoproteins.

4 Claims, No Drawings

METHOD OF TREATING ABNORMAL LIPOPROTE IN RATIOS

CROSS-REFERENCE

This is a continuation-in-part of Ser. No. 9,134 filed Feb. 5, 1979 now abandoned.

DETAILED DESCRIPTION

β-Hydroxy-γ-trimethylaminobutyric acid is a well known compound, also known as carnitine, which has been safely used for a number of years for different indications. For example, the compound is sold in Europe as an appetite stimulant, and it has been reported that the material has an effect on the growth rate of children; see e.g. Borniche et al., Clinic Chemica Acta, 5, 171–176, 1960 and Alexander et al., "Protides in the Biological Fluids", 6th Colloquium, Bruges, 1958, 306–310. Investigation of the drug as an antagonist of thyroid hormone in cases of hyperthyroidism has also been reported, Gilgore et al., Journal of New Drugs, 6, No. 6, 319–320 (1966) and DeFelice et al., loc. cit., 6, No. 6, 315–353 (1966). U.S. Pat. No. 3,830,931 describes improvements in myocardial contractility and systolic rhythm in congestive heart failure which can often be obtained through administration of carnitine. U.S. Pat. No. 3,968,241 describes its use in cardiac arrhythmia. U.S. Pat. No. 3,810,994 describes the use of the compound in the treatment of obesity. Gemelli et al., Boll. Soc. Ital. Bio. Sper. 1974, 50(10), 667-672, reported a decrease in plasma cholesterol and lipoprotein levels in healthy infants upon administration of carnitine, although Strack et al., "Protides of the Biological Fluids", 7th Colloquium, Bruges 1959, 263–267, found an increase in cholesterol levels upon administration while Frohlich et al., Metabolism 27 (5) 1978, 555–561 found no significant change in cholesterol or triglyceride levels upon administration to fasting mature and healthy humans.

Carnitine is normally present in the body where it exerts the function of a carrier of activated long-chain free fatty acids through the mitochondrial membrane. Since the mitochondrial membrane is impermeable to acyl CoA derivatives, long-chain free fatty acids can enter only when esterification with carnitine has taken place. The carrier function of carnitine is exerted both by transporting active long-chain fatty acids from the sites of their biosynthesis, for example the microsomes, to the mitochondria where they are oxidized, and by transporting acetyl CoA from the mitochondria, wherein it is formed, to the extramitochondrial sites where the synthesis of long-chain fatty acids occurs, e.g. in the microsomes wherein acetyl CoA can be utilized for synthesizing cholesterol and fatty acid.

A high level of cholesterol and cholesterol precursors such as triglycerides in the plasma, generally characterized as hyperlipodemia, has long been associated with the etiology of vascular conditions such as infarctions, cardiac ischemia, cerebral ischemia and peripheral vascular diseases and various drugs such as nicotinic acid and its derivatives, triparanol, clofibrate and dexthrothyroxine have been used for the treatment of hyperlipodemia. It has been found, however, that they do not afford constantly reliable therapeutic results, they are generally toxic, particularly in long-term treatment, and exhibit untoward side-effects. For instance, clofibrate has side effects including nausea, gastrointestinal discomfort, drowsiness, headache, and dizziness. Weight gain, myalgia, pruritus, skin rashes, alopecia, and leucopenia also have been reported. Triparanol similarly demonstrates side effects to the extent it has been withdrawn from general clinical use.

The report of Gemelli et al., supra, that carnitine lowers plasma cholesterol levels in healthy infants is, as noted, not readily reconciled with the work of Strack et al., supra, and Frohlich et al., supra. It has been found for example that, in agreement with Gemelli et al., in normal rats, after a single administration of carnitine at dose levels of 50-100 mg/kg and 400 mg/kg orally, intraperitoneally, intravenously and subcutaneously, cholesterol plasma levels were reduced. However in contrast to the findings of Gemelli et al. where the level of triglycerides and free fatty acids were not affected, it has been found that a decrease in triglycerides and free fatty acids does occur upon the administration of carnitine. Moreover and quite surprisingly it has been found that the level of certain fractions of lipoproteins are actually increased upon administration of carnitine and that it is the relative level of these in the plasma rather than the gross level of plasma cholesterol which is therapeutically significant. In fact, a mere reduction in gross plasma cholesterol levels may be detrimental, as is discussed in greater detail hereafter.

Three distinct fractions of plasma lipoprotein can be detected by precipitation method [see Burstein et al., La presse Medicale 43, 974 (1958)] and reckoned as percent of of total cholesterol. These are identified as high density lipoprotein, (HDL), low density lipoprotein (LDL) and very low density lipoprotein (VLDL). It now appears that while cholesterol is bound to lipoproteins of each fraction, conditions leading to vascular problems and which appeared grossly to be hypercholesterolemic are in fact an imbalance in the ratio of these fractions, specifically an abnormally high ratio of (LDL+VLDL)/HDL levels. Mere reduction in overall cholesterol levels does not mean this imbalance is corrected (and indeed it may be aggravated) since a reduction in HDL bound cholesterol without a greater decrease in LDL-bound and VLDL-bound cholesterol would increase the imbalance.

The present invention is based on the discovery that carnitine will increase the level of high density lipoprotein so as to selectively reduce the ratio of low density and very low density lipoproteins in patients in which that ratio is abnormally high. As has been noted, it is the abormal ratio which leads to conditions such as infarction, cardiac ischemia, cerebral ischemia and peripheral vascular diseases, not the mere presence of high levels of cholesterol.

This effect can be observed in recognized experimental models.

For example in the hypercholesterolemic diet fed rat (Nath et al., J. of Nutr. 1959, 67 289), administration of 200 mg/kg of L-carnitine effected about a 24% reduction in serum cholesterol. Significantly however while this was matched by a reduction of about 12% in low density and very low density lipoproteins, the level of high density lipoproteins actually increased by 76%. This increase in HDL levels thus decreased the (LDL+VLDL)/HDL ratio from 7.82 to 3.83. (A typical normal ratio in the same species fed a normal diet was 1.38). These data can be summarized as follows:

TABLE I

Effect of L-carnitine on plasma cholesterol levels and lipoproteins
in hypercholesterolemic diet fed rats.
Mean values ± SEM after 7 days of diet and treatment 200 mg kg$^{-1}$ kp each day.

| treatment | mg kg$^{-1}$ | diet | serum cholesterol mg/100 ml | lipoproteins HDL % | VLDL + LDL % | (LDL + VLDL)/HDL |
|---|---|---|---|---|---|---|
| Saline | — | normal | 75.29 ± 2.20 | 45.6 | 54.38 | 1.38 |
| Saline | — | hyperchol. | 130.46 ± 3.58 | 12.8 | 87.17 | 7.82 |
| Carnitine | 100 × 2 | hyperchol. | 98.61 ± 2.73* | 22.61 | 76.80 | 3.83 |

*P ≦ .01 (Student's "t" test), N = 10

It appears the ability to reduce abnormally high (LDL+VLDL)/HDL ratios is largely restricted to the L-isomer. Thus while the D,L-carnitine racemate can be administered and will increase the HDL level, thus decreasing the (LDL+VLDL)/HDL ratio, the effect is largely traceable to the presence of the L-isomer in the racemate.

Moreover, it does not appear that carnitine has any significant effect on triglyceride levels when these are at normal levels. The increase in HDL levels and the reduction of the (LDL+VLDL)/HDL ratio upon the administration of carnitine occurs rather only when the ratio is abnormally high. Typically, a normal ratio in man is about 1.5–2.7.

As can be seen, administration of carnitine (D,L) at a 1000 mg in a multiple dose regimen of 500 mg b.i.d. to hyperlipodemic patients for 28–30 days effected a reduction in the (LDL+VLDL)/HDL ratio from 3.4±0.12 to 2.8±0.89, a decrease of 16.7%. This reduction was accompanied by reductions of 20.6% total lipids, 10.5% cholesterol and 12.8% triglycerides.

TABLE II

Effect of D,L-carnitine administered in two doses of 500 mg each daily for 28–30 days
on total lipid, triglyceride and cholesterol levels and on the lipoprotein ratio in
patients affected by hyperlipodaemias.
Mean values ± SEM of total lipids (mg/100 ml), triglycerides (mg/100 ml),
cholesterol (mg/100 ml) and LDL/HDL ratio.

| | total lipids mg/100 ml | % | cholesterol mg/100 ml | % | triglycerides mg/100 ml | % | VLDL + LDL/HDL ratio | % | age |
|---|---|---|---|---|---|---|---|---|---|
| before treatment | 855.0 ± 37.92 | | 250.0 ± 8.67 | | 190.38 ± 7.89 | | 3.4 ± 0.12 | | |
| after treatment | 678.5 ± 21.82* | −20.6 | 223.7 ± 7.58** | −10.5 | 165.9 ± 7.34** | −12.8 | 2.8 ± 0.89* | −16.7 | 58.4 |

** and *P ≦ 5% and 1% (Student's "t" test) versus values before treatment. N = 10

In actual practice, carnitine is administered parenterally or orally in any of the usual pharmaceutical forms. These include solid and liquid oral unit dosage forms such as tablets, capsules, powders, solutions, syrups and the like, including sustained release preparations, and fluid injectable forms such as sterile solutions and suspensions. The term unit dosage form as used in this specification and the claims refer to physically discrete units to be administered in single or multiple dosage, each unit containing in association with the carrier, the predetermined quantity of carnitine, or an equivalent amount of a pharmaceutically acceptable salt thereof, calculated to produce the desired effect upon administration of a specific number, one or more, of such units.

The dose which is administered should be determined having regard to the age, weight and condition of the patient, using sound professional judgment. Although effective results can be noticed at doses as low as from 5 to 8 mg/kg of body weight daily, a dose of from about 10 to about 50 mg/kg of body weight daily is preferred. Should it be deemed necessary, larger doses can be safely administered because of the extremely low toxicity of carnitine and its derivatives. In view of the nature of the desired biochemical response, it is often desirable to divide the daily dosage into a several administrations, utilizing a multidose regimen, the response being gauged in view of the total amount administered.

Typical examples of compositions for oral and parenteral administration are as follows:

EXAMPLE 1

Solution or sterile aqueous solutions in concentrations from 50 mg to 500 mg per ml.

A. An injectable composition (for ampoules/vials) is prepared as follows:
L-carnitine: 50 mg
Water for injections: q.s    1 ml B. An intravenous composition is prepared in accordance with the following:
L-carnitine: 50 g
NaCl: 8.6 g
KCl: 0.3 g
CaCl$_2$: 0.33 g
Water for injections: q.s.    1 liter C. A composition for oral use is prepared in accordance with the following non-limitative composition:
L-carnitine: 5 g
Mannitol: 1.1 g
Sorbitol: 60 g
Methyl p-oxy benzoate: 0.100 g
Propyl p-oxy benzoate: 0.050 g
Orange extract: 20 g
Vitamin B$_{12}$: 300 mcg
Purified water: q.s.    100 ml

EXAMPLE 2

Tablets containing from 200 mg to 400 g of L-carnitine are prepared in accordance with the following:
L-carnitine: 200 g
Starch: 100 g
Avicel: 150 g
Talc: 50 g The ingredients are thoroughly mixed and compressed into tablets of 0.1 g. weight.

EXAMPLE 3

Capsules containing from 500 mg of L-carnitine can be prepared without excipients or by admixture with an inert carrier and by introduction into a gelatine sheath.

What is claimed is:

1. The method of increasing the level of high density lipoproteins so as to selectively reduce the ratio of (a) low density and very low density lipoproteins to (b) high density lipoprotein in the plasma of a patient in which said ratio is abnormally above a normal range of about 1.5 to 2.7 which comprises orally or parenterally administering to said patient in a single or multiple dose administration regimen an amount of L-carnitine or a pharmaceutically acceptable salt thereof which is sufficient upon administration according to said regimen to reduce said abnormally high ratio.

2. The method according to claim 1 wherein the total amount administered per day is from about 5 to about 50 mg of carnitine, or an equivalent amount of a salt thereof, per kilogram of body weight.

3. The method according to claim 2 wherein the total amount administered per day is from about 10 to about 50 mg of carnitine, or an equivalent amount of a salt thereof, per kilogram of body weight.

4. The method according to claim 1 wherein carnitine or said salt is administered orally.

* * * * *